United States Patent [19]

Baumgartner

[11] 4,408,082

[45] Oct. 4, 1983

[54] OXIDATION OF ISOBUTANE IN THE DENSE PHASE AND AT LOW OXYGEN CONCENTRATION

[75] Inventor: Herman J. Baumgartner, Houston, Tex.

[73] Assignee: Shell Oil Company, Houston, Tex.

[21] Appl. No.: 308,630

[22] Filed: Oct. 5, 1981

[51] Int. Cl.³ .......................................... C07C 179/02
[52] U.S. Cl. .................................. 568/571; 568/565
[58] Field of Search ................................ 568/571, 565

[56] References Cited

U.S. PATENT DOCUMENTS

| | | | |
|---|---|---|---|
| 2,845,461 | 7/1958 | Winkler et al. | 568/571 |
| 3,478,108 | 11/1969 | Grane | 568/571 |
| 3,502,740 | 3/1970 | Zajacek et al. | 568/571 |
| 3,816,540 | 6/1974 | Barone et al. | 568/571 |
| 3,855,314 | 12/1974 | Dubois et al. | 568/571 |
| 3,907,902 | 9/1975 | Grane | 568/571 |
| 3,974,228 | 8/1976 | Barone | 568/571 |
| 4,128,587 | 12/1978 | Jubin | 568/571 |

FOREIGN PATENT DOCUMENTS 7709269 5/1978 Netherlands .................... 568/571

OTHER PUBLICATIONS

Winkler "Industrial & Engineering Chemistry", vol. 53, (1961), p. 655.

*Primary Examiner*—Werren B. Lone
*Attorney, Agent, or Firm*—Richard F. Lemuth

[57] ABSTRACT

In the direct oxidation of isobutane with molecular oxygen at moderate isobutane conversion levels (up to about 20%) in a reaction mixture maintained at a pressure greater than its critical pressure and at a temperature in the range from about 140° C. to 170° C., the selectivity of the isobutane conversion to tertiary-butyl hydroperoxide is enhanced with only minimal impact on the reaction rate by controlling the oxygen concentration in the reaction mixture at a level below about 0.1%M.

8 Claims, No Drawings

OXIDATION OF ISOBUTANE IN THE DENSE PHASE AND AT LOW OXYGEN CONCENTRATION

BACKGROUND OF THE INVENTION

This invention relates to an improved process for the production of tertiary-butyl hydroperoxide. More particularly, this invention is directed to an improvement in the preparation of tertiary-butyl hydroperoxide by direct, non-catalytic oxidation of isobutane in a reaction mixture at a pressure above the critical pressure of the mixture and at a temperature in the range of about 140° to 170° C., wherein the selectivity with which isobutane is converted to tertiary-butyl hydroperoxide is optimized by controlling the oxygen concentration in the peroxidation reaction zone at critically low levels.

Tertiary-butyl hydroperoxide (hereinafter sometimes referred to as TBHP) is a material of commerce having application as a catalyst, as an initiator for free radial-type reactions and as a starting material or intermediate in the production of valuable chemicals such as oxirane compounds and other organic hydroperoxides.

Because of the ready availability and low cost of starting materials, significant effort has been focused in the past specifically on the preparation of TBHP by direct oxidation of isobutane. Previous disclosures in this area of technology have recognized that the reaction between isobutane and molecular oxygen is inherently nonselective in that significant amounts of tertiary-butyl alcohol and minor amounts of other oxygenated compounds such as acids, aldehydes, ketones and other alcohols are formed in addition to the desired TBHP. According to the work of Winkler et al. (U.S. Pat. No. 2,845,461 and also "Liquid Phase Oxidation of Isobutane", Industrial and Engineering Chemistry, vol. 53 (August, 1961), page 655) the formation of by-products other than the desired TBHP is promoted by the presence of substantial amounts of isobutane in the vapor phase during the course of the oxidation reaction. The oxidation of isobutane had therefore been conducted in the vapor phase in the presence of a catalyst, particularly hydrogen bromide, at lower rate to produce a mixture containing unacceptably large quantities of by-products, and contaminated with catalyst derivatives, e.g., organic bromides. It is taught by Winkler et al that a reaction product consisting essentially of TBHP and tertiary-butyl alcohol can be obtained in high yield by reacting isobutane with molecular oxygen in the liquid phase of a two phase (vapor and liquid) mixture at a temperature of from about 100° to 150° and a pressure of at least 400 psig (up to 700 psig) provided the reaction is carried out in a reaction medium in which the presence of any substantial amount of metal ions is excluded and wherein at least a substantial part of the isobutane is in the liquid phase. Oxidation of isobutane in the liquid phase, generally according to the teachings of Winkler et al, is believed to be a current standard for practice in the art.

In spite of its commercial acceptance, the oxidation of isobutane in the liquid phase remains an inefficient method for preparation of TBHP. For instnace, the reaction is one of low rate, generally requiring a reaction time of several hours. Furthermore, it is recognized that under any given reaction conditions there inherently exists an inverse relationship between isobutane conversion and TBHP selectivity, so that an increase in one is associated with a decrease in the other.

The art contains a number of disclosures of methods for improving some aspect of the overall liquid phase oxidation process. Winkler et al. teach that the oxidation reaction rate in the liquid phase can be enhanced by carrying out the oxidation above the critical temperature of isobutane (134° C.). However, for practice at such elevated temperatures it is necessary that the reaction be conducted in a liquid medium based upon a relatively high boiling point solvent. At temperatures above the critical temperature of isobutane, but below the critical temperature of the reaction mixture, a liquid-phase oxidation can be accomplished. The use of externally-supplied reaction solvents, e.g., organic acids, is discouraged by Winkler et al as tending to increase the complexity of the oxidation reaction and subsequent product separation and recovery. Winkler et al instead propose oxidation above 134° C. in a liquid mixture in which the reaction products, principally tertiary-butyl alcohol and TBHP, act as solvent. However, in comparison with lower temperature liquid-phase oxidation, such practice is said to adversely influence the yield of TBHP. Moreover, it is taught that action in the liquid phase, at a temperature above 134° C., and without an external supply of solvent, requires that the liquid reaction mixture have a composition corresponding to a conversion of isobutane of at least 20% and preferably of more than 30%. Because of the recognized inverse relationship between isobutane conversion and selectivity to TBHP, isobutane oxidation at a temperature above 134° C. according to these teachings is a process in which selectivity to TBHP is inherently limited. Furthermore, enhanced rate in such a process is in large degree the result of the high conversions achieved—since TBHP is itself an initiator for isobutane oxidation, the rate of conversion increases as the concentration of TBHP in the reaction mixture increases. On the whole, the liquid phase oxidation reaction of Winkler et al., even above the 134° C. critical temperature of isobutane, remains a process characterized by a relatively slow rate of reaction and a low selectivity for TBHP.

The relevant art also provides disclosure of more recent work relating to improving the conversion or selectivity of non-catalytic liquid-phase isobutane oxidation. For instance, U.S. Pat. No. 3,478,108 to Grane describes the effects of the addition of minor amounts of water (up to 6 percent) upon the conversion and selectivity in the liquid phase oxidation of isobutane with molecular oxygen to afford TBHP and tertiary-butyl alcohol in accordance with the reaction conditions generally described by Winkler et al.

Further, U.S. Pat. No. 3,907,902 to Grane discloses that the selectivity with which isobutane is converted to TBHP in the direct oxidation reaction can be enhanced by the addition of small amounts of certain alcohols (isopropyl alcohol) to the oxidation reaction zone wherein molecular oxygen is reacted with isobutane, again according to the general conditions described by Winkler et al. Practice according to such methods, however, may prove undesirable, for like the use of externally-supplied reaction solvents disclosed by Winkler et al. addition of foreign substances to the reaction mixture may have adverse effect upon the complexity of the reaction and the subsequent product recovery. Furthermore, the greatest benefits of these processes, with respect to enhanced selectivity, for instance, are realized at relatively low temperature, e.g., about 134° C. or less.

In the commonly assigned, copending application of E. G. Foster and E. F. Lutz, entitled Oxidation of Isobutane under Supercritical Conditions, Ser. No. 308,631, filed on even date herewith, it is disclosed that the production of TBHP per unit of reactor volume per unit of time can be substantially enhanced by conducting isobutane oxidation at least in part in a supercritical reaction mixture at a reaction temperature above the critical temperature of the mixture, at a reaction pressure above the critical pressure of the mixture, and under conditions relating to composition of the mixture.

SUMMARY OF THE INVENTION

It has now been found that the selectivity with which isobutane is converted to TBHP in the direct, noncatalytic reaction of isobutane with molecular oxygen can be enhanced in a process which comprises reacting the isobutane with the oxygen in a dense phase reaction mixture at a reaction temperature in the range of about 140° C. to 170° C. and at a reaction pressure above the critical pressure of the reaction mixture, by limiting oxygen content of the reaction mixture to a low concentration, while controlling the isobutane conversion at a moderate level.

In particular, the essence of this invention is the discovery that maintaining an oxygen concentration in the dense phase reaction mixture below 0.1 percent by mol (%M) will afford a highly selective conversion of isobutane to TBHP with only minimal impact on the excellent conduction rate for TBHP that is generally characteristic of isobutane oxidation in the dense phase. The discoveries of Foster and Lutz, as described in the referenced copending application, are directed to increasing the production of TBHP per unit of reaction mixture volume per unit of time by oxidation under like conditions of temperature and pressure. The present invention, on the other hand, accomplishes both an enhanced production rate for TBHP by operation in the dense phase and also an enhanced selectivity to TBHP by operation at critically low oxygen concentration. At a given conversion of isobutane, there is achieved by practice of the process of this invention a selectivity to TBHP that is substantially greater than that associated with isobutane oxidation either in the liquid phase or in the dense phase at oxygen concentration above the low levels now specified.

For the purposes of the present invention it is necessary to maintain reaction temperature in the range of about 140° to 170° C. and reaction pressure above the critical pressure of the reaction mixture (and above about 900 psig), and overall isobutane conversion in the reaction mixture between about 5 and 20%. Preferably, the reaction temperature at which the process improvement of the invention is carried out is, at least during part of the reaction, greater than the critical temperature of the reaction mixture.

The finding that enhanced selectivity in the oxidation of isobutane to TBHP results from control of oxygen concentration in the reaction mixture is considered especially surprising in that the low oxygen concentration is typically achieved, at least in part, by increasing the reaction residence time. Since longer residence times prolong the exposure of the thermally unstable TBHP product to high temperatures, it might be expected that the selectivity with which isobutane is converted to TBHP would be reduced by thermal decomposition of TBHP under such conditions.

A particularly significant aspect of the enhanced selectivity for TBHP associated with the invention is a discovery of substantial reduction of the make of acids (primarily formic acid) in the reaction mixture. It is believed that this reduction in acid make in turn results in a reduction of the propensity of product TBHP to undergo acid-catalyzed decomposition.

DESCRIPTION OF THE PREFERRED EMBODIMENT

In the process according to the present invention, isobutane oxidation is carried out at tempratures and pressures significantly above the critical temperature (135° C.) and pressure (525 psig) for isobutane, and also necessarily above the critical pressure of the mixture in which the reaction takes place. At the temperature and pressure conditions employed, the reaction mass, comprising reactants and reaction products, is a single, dense, quasi-liquid phase. General characteristics of isobutane oxidation under such conditions are described in the aforementioned application of Foster and Lutz, the teachings of which are incorporated herein by reference. For particular purposes of this invention, reaction temperatures in the range from about 140° C. to 170° C. and pressures above 900 psig are suitably employed. Preferably the reaction temperature is in the range of about 145° to 160° C. with temperatures of from about 150° to about 155° C. being most preferred. Similarly, the reaction pressure (combined partial pressures of reactants and reaction products) is preferably in the range of about 900 to 1500 psig with pressures in the range of about 950 to 1100 psig being most preferred. A particularly preferred set of reaction conditions for the direct oxidation of isobutane in accordance with the invention includes a reaction temperature of about 155° C. and a reaction pressure of about 1000 psig.

The isobutane subject to direct oxidation in accordance with the invention is suitably substantially pure, that is free of other hydrocarbons and metal ion contaminants. The molecular oxygen employed as a reactant in the process is preferably substantially pure oxygen, such as is obtainable from a variety of commercial sources.

An essential aspect of the present invention is the maintenance of a critically low oxygen concentration in the reaction mixture in which the isobutane oxidation reaction takes place. Maintenance of the oxygen concentration at a level below 0.1%M in the reaction zone of the direct oxidation according to the invention affords a significant increase in the selectivity with which isobutane is converted to TBHP over that obtained at higher oxygen concentrations when the overall isobutane conversion in the reaction is controlled at a moderate level (less than about 20% conversion). Further in the process of the invention this enhanced selectivity is obtained without sacrificing the benefits of the higher TBHP production rates characteristic of operation above the critical temperature and pressure of the reaction mixture. That is, while there is some decrease in the production for TBHP attributable to the lower concentration of oxygen reactant, the reaction rate is still significantly higher than that obtained in direct oxidations under liquid phase processes of the prior art. Preferably, the oxygen concentration is maintained at a level of less than about 0.5% M in the reaction mixture of the direct oxidation according to the invention, with oxygen concentrations of less than 0.3% M being most preferred. Concentrations as low as 0.005% M are suitable for purposes of the invention. Still lower concentrations are also believed to be suitable, although in practice it is very difficult to maintain such concentrations uniformly throughout the reaction mixture.

The critically low oxygen concentrations required in the direct isobutane oxidations according to the invention are achieved through the control of several process parameters including reactant molar charge ratios, reaction residence times, reaction temperatures, reaction mixture agitaton and the rate of reactant addition to the reaction mixture. The adjustment and control of all of these factors to achieve the desired oxygen concentration in the reaction zone is within the general level of skill in te art, however, the more important factors will be highlighted below.

Isobutane oxidation in the dense phase is necessarily conducted in a mixture comprising isobutane reactant in such a quantity that the isobutane partial density, i.e., the weight of isobutane per unit volume of reaction mixture, is greater than about 12 lb/ft$^3$. Preferably, isobutane partial density in the reaction mixture is in the range of from about 15 to 35 lb/ft$^3$, while a range of about 18 to 30 lb/ft$^3$ is more preferred, and a range of about 19 to 25 lb/ft$^3$ is most preferred.

The direct oxidation of isobutane in accordance with the invention may be suitable carried out in batch or continuous fashion. In cases where the oxidation is conducted batchwise, the isobutane reactant is initially charged into an agitated reaction vessel equipped with external cooling and the oxygen is added incrementally to the isobutane at a controlled rate dependent on the rate of oxygen consumption such that the oxygen concentration in the reaction mixture does not exceed the aforementioned concentration limits. To insure a uniform oxygen concentration throughout the reaction mixture, it is preferable to add the oxygen by means of multiple spargers spaced in the lower portions of the reaction vessel. Further, in view of the importance of reaction zone mixing in avoiding localized excesses of oxygen over the desired concentration, it is desirable to employ mechanical agitation coupled with appropriate internal baffles to insure turbulent flow in the reactor. The process according to the invention is preferably carried out continuously in one or more reaction stages, most preferably two or three stages, with all of the isobutane being added to the first reaction stage and the oxygen reactant supply being split between the several stages. A particularly preferred continuous process of this sort is that described in the commonly-assigned copending application of E. G. Foster, entitled An Improved Process for Oxidation of Isobutane, Ser. No. 308,629, filed on even date herewith.

The process according to the invention is effective in enhancing the selectivity with which isobutane is converted to TBHP provided the overall conversion of isobutane to reaction products is maintained at a level below about 20%. While there is no lower limit on the overall isobutane conversion insofar as enhanced selectivity to TBGP is concerned, lower isobutane conversions in fact giving even higher selectivities to TBHP, practical consideration such as equipment sizing, dictate that the overall isobutane conversion should be at least about 5%. Preferably, the overall isobutane conversion is maintained between about 7 and about 15% and most preferably from about 8 to about 10%. This overall isobutane conversion is achieved (as is the critically low oxygen concentration) through the control of several factors which will be apparent to those skilled in the art including reactant molar charge ratios, reaction temperature and reaction residence times. Typically, the isobutane and oxygen reactant will be charged to the reaction mixture of the process according to the invention at an isobutane to oxygen molar ratio of from about 5:1 to about 20:1. Preferably, the molar charge ratio of isobutane to oxygen is between about 8:1 to about 12:1. The residence time employed is dependent on the specific reaction temperature used since reaction rate increases with increasing reaction temperature and thus, at the highest reaction temperature within the range permitted by the process of the invention less reaction zone residence time is necessary to achieve the desired isobutane conversion. Most commonly, the reaction zone residence time in the process of the invention will range from about 15 to about 80 minutes.

The reaction product of the process of the invention will typically contain about 4 to 12%w TBHP, about 2 to 7%w tertiary-butyl alcohol and 70 to 90%w isobutane along with minor amounts of water and other oxygenated organic compounds (acids and alcohols). This reaction product can be further processed using conventional techniques (multiple fractionations and carbonate wash) to remove the residual isobutane and reaction by-products to afford a TBHP concentrate which is suitable for use as a reactant in other chemical synthesis, for example, olefin epoxidation.

The preparation of TBHP by direct oxidation of isobutane in accordance with the invention will be further described in the following illustrative embodiments.

ILLUSTRATE EMBODIMENTS I-XV

Isobutane was oxidized with molecular oxygen in a series of comparative experiments using a one-liter continuous reactor under reaction conditions both according to the invention and not according to the invention. In these experiments, the reactant flow rates and reaction residence times were controlled at three different reaction temperature levels (145°, 150° and 155° C.) to afford oxygen concentrations in the reaction zone within the critical limits of the invention for those experiments carried out according to the invention while higher reaction zone oxygen concentrations were employed in the comparative experiments (not according to the invention).

The apparatus employed in this test program included a one-liter 304 stainless steel autoclave equipped with a turbine impeller and top inlets for isobutane and molecular oxygen as well as a top outlet for reaction product. The autoclave was also equipped with a cooling jacket for temperature control during the exothermic oxidation reaction. Molecular oxygen (99.9%w) and isobutane (99.6%w) were metered at controlled rates into the autoclave, stirred at 1000 rpm by the turbine impeller, and reaction product was continuously withdrawn from the autoclave at an equivalent rate; the rate of reactant introduction and reaction product withdrawal being set in each case to afford the desired oxygen concentration and residence time in the reaction zone. Upon removal from the reactor, the reactor effluent was reduced to near atmospheric pressure and the less volatile reaction products were condensed at −1° C. The entire reaction product including the condensed phase was then passed to a separation zone (304 stainless steel cylindrical tank operated at 2° C. and 5 psig) wherein the bulk of the unreacted isobutane and other non-condensable gases were separated from the liquid products. The separated gaseous phase is taken overhead from the separator and passed through a knock back condenser (−10° C.) to remove any entrained condensables which drain back into the separator. The liquid product in the separator was passed by bottom drain to a stripping column to remove the remainder of the unreacted isobutane. This stripping column consisted of an eight inch glass tube filled with cannon packing and heated electrically to 35° C. at the bottom. A warm nitrogen gas stream was passed counter-currently up the column to aid in disengaging the isobutane. The vents from the condenser and the stripping column were combined and passed through a continuous oxygen analyzer and a dry test meter prior to disposal. Mass spectral and gas chromatography analyses were also performed on the vent stream prior to its disposal. The TBHP in the liquid product was measured by gas chromatography while the total acids were determined using titration with sodium hydroxide. Other organics and water were determined in the liquid product by gas chromatography. Water was determined by titration (Karl Fischer).

The results of the experiments and further details on the reaction conditions employed are listed in the tables below. All of the reactions were carried out at a reactor pressure of about 1000 psig. The reaction zone residence times given are those measured after the reaction reached steady state operation (typically 1 to 3 hours after start up). In view of the nature of the reaction system, it is considered that the oxygen concentration of the reactor effluent reasonably approximates the oxygen concentration in the reaction zone. The reported reaction product selectivities based on the isobutane charge were determined using the following formula:

$$\text{percent selectivity} = \frac{\text{moles of identified component in reaction product}}{\text{moles of isobutane converted in the reaction}} \times 100$$

TABLE I

Isobutane Oxidation According To The Invention

| Illustrative Embodiment | 1 | 2 | 3 | 4 | 5 | 6 | 7 | 8 | 9 |
|---|---|---|---|---|---|---|---|---|---|
| Reaction Temperature °C. | 155 | 155 | 150 | 155 | 150 | 145 | 155 | 150 | 145 |
| Molar Ratio Isobutane/$O_2$ | 11.9 | 11.1 | 11.0 | 12.1 | 10.7 | 10.7 | 6.6 | 7.3 | 7.4 |
| Isobutane Flow (g-mol/liter/hr) | 10.4 | 7.52 | 7.43 | 4.58 | 4.62 | 4.58 | 4.32 | 4.56 | 4.51 |
| $O_2$ Flow (g-mol/liter/hr) | 0.873 | 0.676 | 0.674 | 0.380 | 0.433 | 0.429 | 0.660 | 0.627 | 0.611 |
| Residence Time (min.) | 33.4 | 43.8 | 44.4 | 72.2 | 70.9 | 71.6 | 72 | 69.1 | 70.0 |
| $O_2$ Concentration In Reaction Mass % M | <0.04 | <0.04 | <0.04 | <0.04 | <0.04 | <0.04 | <0.04 | <0.04 | <0.04 |
| Isobutane Conversion % | 8.8 | 8.8 | 9.2 | 8.9 | 8.9 | 9.3 | 15.4 | 13.5 | 13.0 |
| TBHP Production (g-mol/liter/hr) | 0.501 | 0.401 | 0.439 | 0.262 | 0.282 | 0.267 | 0.382 | 0.378 | 0.348 |
| Selectivity To TBHP | 56.6 | 62.0 | 63.9 | 64.8 | 68.7 | 62.5 | 57.3 | 61.6 | 59.9 |
| Tertiary-butyl Alcohol | 39.7 | 33.2 | 30.9 | 29.8 | 27.7 | 30.9 | 37.2 | 34.0 | 35.8 |
| Di-tert-butyl Peroxide | 0.37 | 0.25 | 0.20 | 0.49 | 0.29 | 0.43 | 0.43 | 0.37 | 0.23 |
| Acetone | 2.48 | 2.50 | 2.34 | 2.67 | 1.51 | 1.83 | 3.32 | 1.55 | 1.79 |
| Methanol | 1.55 | 0.47 | 0.64 | 0.65 | 0.69 | 0.98 | 0.94 | 0.70 | 0.60 |
| Water | 2.94 | 2.11 | 3.06 | 6.48 | 4.08 | 4.40 | 6.40 | 2.98 | 3.44 |
| Total Acid | 0.98 | 0.85 | 0.86 | 0.70 | 0.54 | 0.61 | 0.90 | 0.83 | 0.70 |
| Isobutyl Alcohol | 1.28 | 0.74 | 0.91 | 0.80 | 0.67 | 0.79 | 0.65 | 0.70 | 0.83 |

TABLE II

Isobutane Oxidation Not According To The Invention

| Illustrative Embodiment | 10 | 11 | 12 | 13 | 14 | 15 |
|---|---|---|---|---|---|---|
| Reaction Temperature °C. | 155 | 155 | 155 | 150 | 146 | 155 |
| Molar Ratio Isobutane/$O_2$ | 7.9 | 8.2 | 10.1 | 9.7 | 13.5 | 6.3 |
| Isobutane Flow (g-mol/liter/hr) | 9.9 | 11.0 | 9.9 | 9.2 | 9.1 | 9.0 |
| $O_2$ Flow (g-mol/liter/hr) | 1.25 | 1.34 | 0.98 | 0.95 | 0.67 | 1.44 |
| Residence Time (min.) | 32.6 | 29.5 | 33.8 | 35.8 | 37.3 | 34.7 |
| $O_2$ Concentration In Reaction Mass % M | 1.05 | 1.1 | 3.2 | 1.0 | 1.1 | 1.0 |
| Isobutane Conversion % | 12.7 | 12.2 | 9.9 | 10.7 | 7.4 | 16.0 |
| TBHP Production (g-mol/liter/hr) | 0.541 | 0.518 | 0.437 | 0.426 | 0.369 | 0.442 |
| Selectivity To TBHP | 43.1 | 38.6 | 44.6 | 43.3 | 54.8 | 30.7 |
| Tertiary-butyl Alcohol | 52.0 | 54.7 | 48.4 | 50.9 | 40.6 | 61.9 |
| Di-tert-butyl Peroxide | 0.17 | 0.14 | 0.17 | 0.16 | 0.20 | 0.13 |
| Acetone | 3.8 | 5.0 | 5.0 | 4.1 | 3.0 | 5.8 |
| Methanol | 3.9 | 3.2 | 5.2 | 2.9 | 1.3 | 4.9 |
| Water | 4.0 | 3.9 | 5.0 | 3.7 | 3.1 | 3.7 |
| Total Acid | 2.0 | 2.0 | 1.8 | 1.8 | 1.1 | 2.4 |
| Isobutyl Alcohol | 1.9 | 1.8 | 1.7 | 1.4 | 1.2 | 1.3 |

A review of the data given in the tables above demonstrates that selectivity to TBHP in the isobutane oxidation reaction generally decreases with increasing isobutane conversion and increasing reaction temperature for both isobutane oxidation according to the invention and isobutane oxidation not according to the invention. However, in comparing similar isobutane conversion levels and reaction temperature between oxidations according to the invention and those not according to the invention, for example, illustrative embodiments 7 and 11, 8 and 13, and 6 and 14, it becomes apparent that oxidation using critically low concentrations of oxygen in the reaction zone affords a significant (8–18 selectivity points) increase in the selectivity with which isobutane is converted to TBHP. Further, while the residence times in the oxidations according to the invention are generally longer than those in the comparative experiments not according to the invention, it is apparent from a comparison of illustrative embodiments 1 and 12 that residence time is not the controlling factor in the achievement of the high selectivities to TBHP which characterize the present invention.

What is claimed is:

1. In a process for the preparation of tertiary-butyl hydroperoxide by the direct oxidation of isobutanes which comprises reacting isobutane with molecular oxygen in a dense phase reaction mixture at a reaction temperature in the range from about 140° C. to 170° C. and at a reaction pressure above the critical pressure of the mixture and above 525 psig, the improvement which comprises limiting the oxygen concentration in the mixture to less than 0.1%M, and controlling said reaction to afford an overall isobutane conversion of from about 5 to about 20%M.

2. The process according to claim 1 wherein the oxygen concentration in the reaction mixture is less than about 0.05%M.

3. The process according to claim 2 wherein the reaction temperature is in the range of about 145° to 160° C. and the reaction pressure is in the range of about 900 to about 1500 psig.

4. The process according to claim 3 wherein the overall isobutane conversion is controlled at between about 7 and about 5%.

5. The process according to claim 4 wherein the reaction temperature is in the range of from about 50° to about 55° C. and the reaction pressure is in the range of about 950 to 1100 psig.

6. The process according to claim 5 wherein the oxygen concentration is maintained at a level of less than about 0.03%M.

7. The process according to claim 6 wherein the overall isobutane conversion is controlled between about 8 and about 10%.

8. The process according to claim 2 in which the reaction of isobutane and molecular oxygen is carried out continuously with a reaction mixture residence time of between about 15 and about 18 minutes.

* * * * *